United States Patent [19]

Nedelec et al.

[11] Patent Number: 4,987,128
[45] Date of Patent: Jan. 22, 1991

[54] NOVEL 10β-ALKYNYL-STEROIDS

[75] Inventors: Lucien Nedelec, Le Raincy; Francois Nique, Pavillons-sous-Bois; Anne-Marie Moura, Paris, all of France

[73] Assignee: Roussel Uclaf, Paris, France

[21] Appl. No.: 18,199

[22] Filed: Feb. 24, 1987

[30] Foreign Application Priority Data

Feb. 24, 1986 [FR] France .................. 86 02510

[51] Int. Cl.$^5$ .................. A61K 31/58; A61K 31/585; C07J 43/00; C07J 33/00
[52] U.S. Cl. .................. 514/175; 514/173; 514/176; 514/178; 540/15; 540/28; 540/29; 540/30; 540/41; 540/44; 552/508; 552/523; 552/553; 552/597; 552/598
[58] Field of Search .................. 260/397.4; 540/15, 28, 540/29, 30, 41, 44; 514/173, 175, 176, 178; 552/508

[56] References Cited

U.S. PATENT DOCUMENTS

3,218,316 11/1916 Edwards .................. 260/397.5
4,464,302 8/1984 Nedelec .................. 260/397.45
4,701,449 10/1987 Torelli et al. .................. 260/397.45

FOREIGN PATENT DOCUMENTS

2078749 1/1982 United Kingdom .

OTHER PUBLICATIONS

Aries, Chem. Abs., 84, 79726g.
Marcolte, Steroids, 39, 2924, (1982).

Primary Examiner—Mark L. Berch
Attorney, Agent, or Firm—Bierman and Muserlian

[57] ABSTRACT

Novel 10β-alkynyl-steroids of the formula

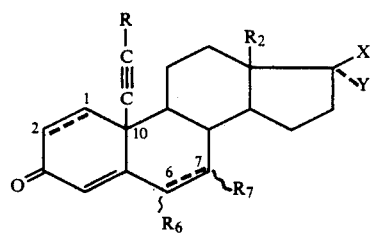

wherein R is selected from the group consisting of hydrogen, optionally substituted alkyl and alkoxy of 1 to 8 carbon atoms, optionally substituted alkenyl and alkynyl of 2 to 8 carbon atoms, optionally substituted aryl and aralkyl, optionally esterified carboxy, dialkylamino with alkyl of 1 to 6 carbon atoms, halogen and trialkylsilyl of 1 to 7 alkyl carbon atoms, $R_6$ and $R_7$ taken together with the carbon atoms to which they are attached form cyclopropyl or $R_6$ is hydrogen and $R_7$ is $R_1$, $R_1$ is selected from the group consisting of hydrogen, optionally substituted alkyl of 1 to 6 carbon atoms, optionally substituted alkenyl and alkynyl of 2 to 6 carbon atoms and acetylthio, $R_2$ is methyl or ethyl, X and Y taken together form a member selected from the group consisting of

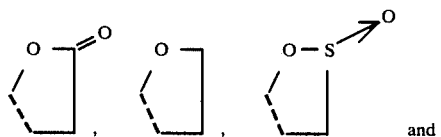

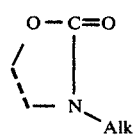

Alk is alkyl of 1 to 8 carbon atoms or X is hydroxy and Y is

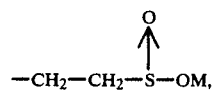

or X is optionally acylated or etherified hydroxy and Y is selected from the group consisting of —CH$_2$—CH$_2$—CH$_2$—OH, hydrogen, R$_4$, and —CH$_2$—CH$_2$—COOM, M is selected from the group consisting of hydrogen, —NH$_4$ and alkali metal and R$_4$ is selected from the group consisting of alkyl of 1 to 6 carbon atoms and alkenyl and alkynyl of 2 to 6 carbon atoms, the dotted lines indicate the optional presence of a second carbon-carbon bond when R$_6$ and R$_7$ and the carbon to which they are attached do not form cyclopropyl and the wavy lines indicate that R$_6$ and R$_7$ may be in the α or β position with the proviso that R is not hydrogen when R$_6$ and R$_7$ are hydrogen, R$_2$ is methyl, X is optionally acylated or etherified hydroxy, Y is hydrogen or R$_4$ and the dotted lines are not a second carbon-carbon bond having aldosterone antagonistic activity and increased hydrosodic diuresis with organic potassium conservation with little secondary hormone effects.

20 Claims, No Drawings

NOVEL 10β-ALKYNYL-STEROIDS

STATE OF THE ART

Related prior art includes U.S. Pat. No. 3,218,316, British Pat. No. 2,078,749, copending U.S. patent application Ser. No. 768,867 filed Aug. 23, 1985 U.S. Pat. No. 4,701,449 and the prior art cited therein and Steroids, Vol. 39, No. 3 (1982), p. 325 to 344.

OBJECTS OF THE INVENTION

It is an object of the invention to provide the novel 10β-alkynyl-steroids of formula I and a process for their preparation.

It is another object of the invention to provide compositions and methods of treating arterial hypertension and cardiac insufficiencies.

These and other objects and advantages of the invention will become obvious from the following detailed description.

THE INVENTION

The novel compounds of the invention are 10β-alkynyl-steroids of the formula

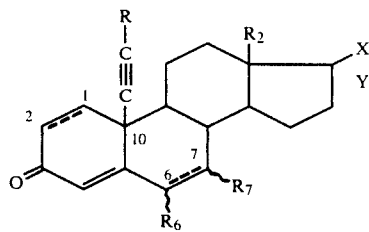

wherein R is selected from the group consisting of hydrogen, optionally substituted alkyl and alkoxy of 1 to 8 carbon atoms, optionally substituted alkenyl and alkynyl of 2 to 8 carbon atoms, optionally substituted aryl and aralkyl, optionally esterified carboxy, dialkylamino with alkyl of 1 to 6 carbon atoms, halogen and trialkylsilyl of 1 to 7 alkyl carbon atoms, $R_6$ and $R_7$ taken together with the carbon atoms to which they are attached form cyclopropyl or $R_6$ is hydrogen and $R_7$ is $R_1$, $R_1$ is selected from the group consisting of hydrogen, optionally substituted alkyl of 1 to 6 carbon atoms, optionally substituted alkenyl and alkynyl of 2 to 6 carbon atoms and acetylthio, $R_2$ is methyl or ethyl, X and Y taken together form a member selected from the group consisting of

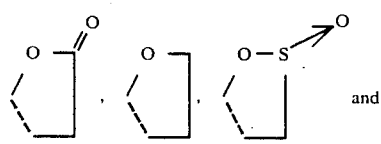

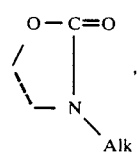

Alk is alkyl of 1 to 8 carbon atoms or X is hydroxy and Y is

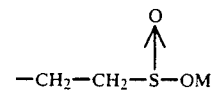

or X is optionally acylated or etherified hydroxy and Y is selected from the group consisting of —CH$_2$—CH$_2$—CH$_2$—OH, hydrogen, $R_4$, and —CH$_2$—CH$_2$—COOM, M is selected from the group consisting of hydrogen, —NH$_4$ and alkali metal and $R_4$ is selected from the group consisting of alkyl of 1 to 6 carbon atoms and alkenyl and alkynyl of 2 to 6 carbon atoms, the dotted lines indicate the optional presence of a second carbon-carbon bond when $R_6$ and $R_7$ and the carbon to which they are attached do not form cyclopropyl and the wavy lines indicate that $R_6$ and $R_7$ may be in the α or β position with the proviso that R is not hydrogen when $R_6$ and $R_7$ are hydrogen, $R_2$ is methyl, X is optionally acylated or etherified hydroxy, Y is hydrogen or $R_4$ and the dotted lines are not a second carbon-carbon bond Among the preferred compounds of the invention are those of the formula

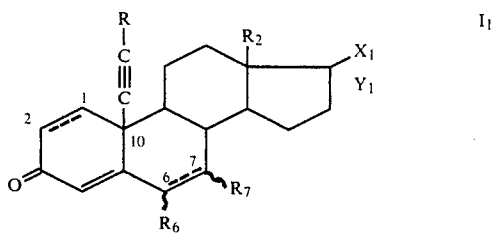

wherein R, $R_6$, $R_7$, $R_2$, the dotted lines and the wavy lines have the above definitions, $X_1$ is an optionally acylated or etherified hydroxy and $Y_1$ is selected from the group consisting of hydrogen, $R_4$, —CH$_2$—CH$_2$—COOM and —CH$_2$—CH$_2$—CH$_2$—OH, M is hydrogen, —NH$_4$ or alkali metal, $R_4$ is selected from the group consisting of alkyl of 1 to 6 carbon atoms and alkenyl and alkynyl of 2 to 6 carbon atoms or $X_1$ and $Y_1$ taken together form

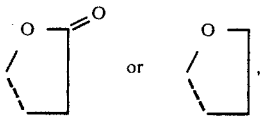

with the proviso that R is not hydrogen when $R_6$ and $R_7$ are hydrogen, $R_2$ is methyl, $X_1$ is optionally acylated or etherified hydroxyl, $Y_1$ is hydrogen or $R_4$ and both the dotted lines are not a second carbon-carbon bond.

Examples of R are alkyl such as methyl, ethyl, isopropyl, n-propyl, butyl, sec-butyl, tert.-butyl and linear and branched pentyl, hexyl, heptyl and octyl; alkenyl such as vinyl, allyl, 1-propenyl and butenyl; alkynyl such as ethynyl, propargyl and butynyl; all of which may be substituted with at least one member of the group consisting of hydroxy; optionally esterified carboxy such as methoxycarbonyl, ethoxycarbonyl; optionally protected amino such as tritylamino, chloroacetylamino, trifluoroacetylamino and trichloroethoxycarbonylamino; mono- and dialkylamino such as methylamino and dimethylamino; and halogen such as chlorine or bromine.

Further examples of R are aryl and aralkyl such as phenyl, benzyl and phenethyl optionally substituted with at least one member of the group consisting of hydroxy, optionally esterified carboxy, —NH$_2$, mono- and dialkylamino such as methylamino and dimethylamino, alkyl such as methyl, alkoxy such as methoxy, alkylthio such as methylthio. R may also be alkoxy such as methoxy, ethoxy, propoxy, isopropoxy and tert.-butoxy and trialkylsilyl such as trimethylsilyl.

The values for R$_1$ and R$_4$ can be selected from those of the illustrated groups of R. M is preferably sodium, potassium or lithium. When X is acylated or etherified hydroxy, it is preferably acetyloxy, propionyloxy, methoxy or ethoxy. When R$_1$ is other than hydrogen, it is preferably in the 7-position. The cyclopropyl formed by R$_6$ and R$_7$ is preferably 6$\beta$, 7$\beta$.

The compounds of formula I wherein X and Y form

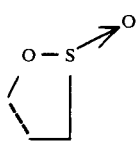

can exist in the form of two diastereoisomers at the sulfur atom and may be separated from each other and are named isomer A and B with isomer A being the isomer with the higher melting point.

Among the further preferred compound of formula I are those of the formula

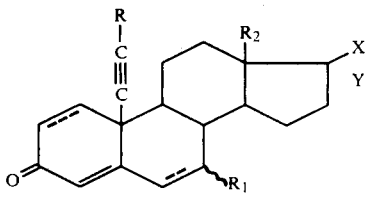

wherein R, R$_1$, R$_2$, X$_1$, Y$_1$, the dotted lines and the wavy lines have the above definitions.

More preferred compounds of formula I are those wherein the substituent which R and R$_1$ can comprise are selected from the group consisting of —OH, optionally esterified carboxy, —NH$_2$, protected amino, halogen and mono- and dialkylamino. Also preferred are the compounds wherein R is hydrogen, alkyl of 1 to 3 carbon atoms, hydroxymethyl or phenyl, those wherein R$_1$ is hydrogen, alkyl of 1 to 4 carbon atoms and acetylthio, those wherein X and Y form

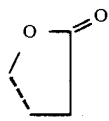

or X is —OH and Y is hydrogen or —CH$_2$—CH$_2$—COOM' and M' is hydrogen or alkali metal.

Most preferred compounds of formula I are those wherein R is hydrogen or methyl, R$_2$ is —CH$_3$ and X and Y form

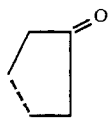

or X is —OH and Y is hydrogen when R is other than hydrogen. Specific preferred compounds are the gamma-lactone of 10$\beta$-ethynyl-17$\beta$-hydroxy-3-oxo-19-nor-17$\alpha$-pregn-4-en-21-carboxylic acid, 17$\beta$-hydroxy-10$\beta$-(1-propynyl)-estr-4-en-3-one and the gamma-lactone of 17$\beta$-hydroxy-3-oxo-10$\beta$-(1-propynyl)-19-nor-17$\alpha$-pregn-4-en-21-carboxylic acid.

The novel process for the preparation of the compounds of formula I comprises reacting a compound of the formula

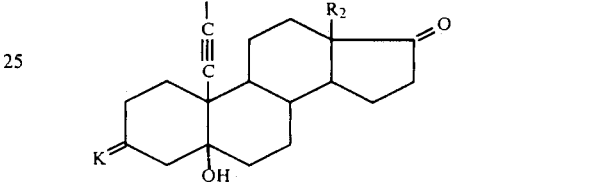

wherein R' has the definition of R with the reactive groups optionally protected, R$_2$ has the above definition and K is a ketone protective group with either a trimethylsulfonium halide in the presence of a strong base and then with a metallic derivative of acetonitrile followed by treatment with a base and then an acid or with a compound of the formula

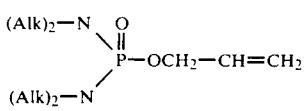

wherein Alk is alkly of 1 to 4 carbon atoms in the presence of a strong base followed by treatment with an acid to obtain a compound of the formula

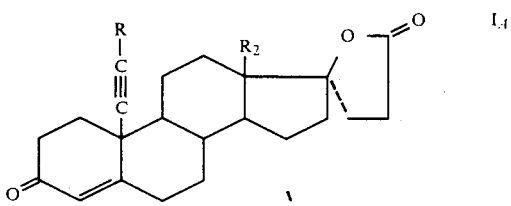

or with a compound of the formula

wherein X is halogen and B is a hydroxy protective group or an alcoholate of magnesium to obtain, after treatment with an acid, a compound of the formula

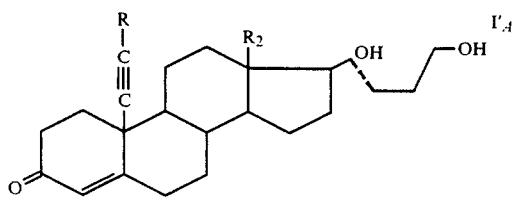

optionally treating the latter with a sulfonic acid halide in the presence of a base to obtain a compound of the formula

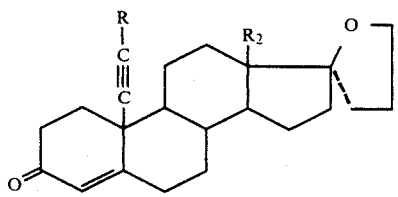

or with a reducing reagent and then with an acid to obtain a compound of the formula

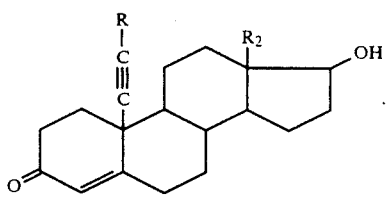

or with an organometallic R₄MgX, X is halogen then with an acid to obtain a compound of the formula

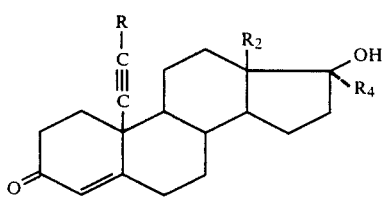

or first with a trimethylsulfonium halide in the presence of a strong base, then with a primary amine of the formula H₂N-alk, alk being defined as above, in the presence of an acid, then with an alkyl chloroformate, with a strong base and finally with an acid, to obtain a compound of the formula

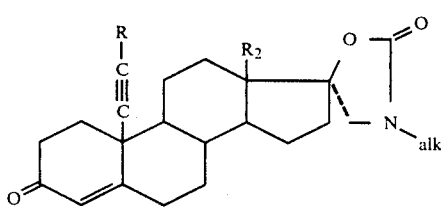

or first with a trimethylsulfonium halide in the presence of a strong base, then by methyl tertbutyl sulfoxide in the presence of n-butyl-lithium to obtain a compound of the formula

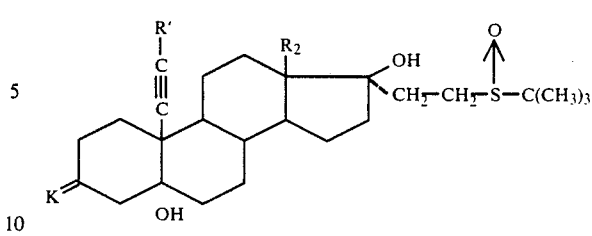

in the form of a mixture of two diastereo-isomers at the level of the sulfur atom, optionally the two diastereo-isomers are separated, then either their mixture, or each of them separately, is reacted with an acid to obtain a compound of the formula

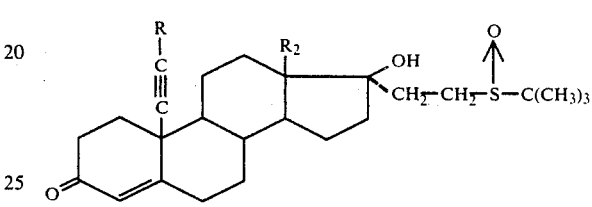

in the form of a mixture of two diastereo-isomers or of one diastereoisomer, if necessary, the two diastereo-isomers are separated, then either mixture, or each of them separately, is reacted with N-chloro-or N-bromo-succinimide to obtain a compound of the formula

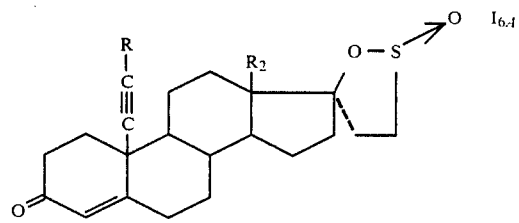

and optionally the compounds of formulae $I_A$, $I_A'$, $I_A''$, $I_{3A}$, $I_{4A}$, $I_{5A}$ and $I_{6A}$ are reacted with an alkyl orthoformate in the presence of an acid, then with a dehydrogenation agent to obtain the following products with the formulae $I_B$, $I_B'$, $I_B''$, $I_{3B}$, $I_{4B}$, $I_{5B}$ and $I_{6B}$

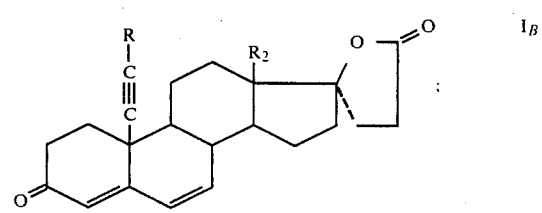

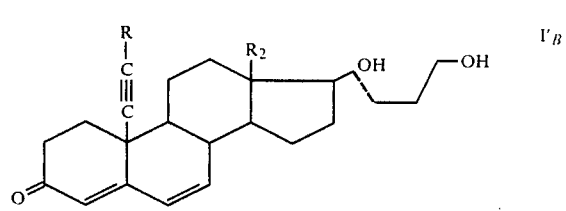

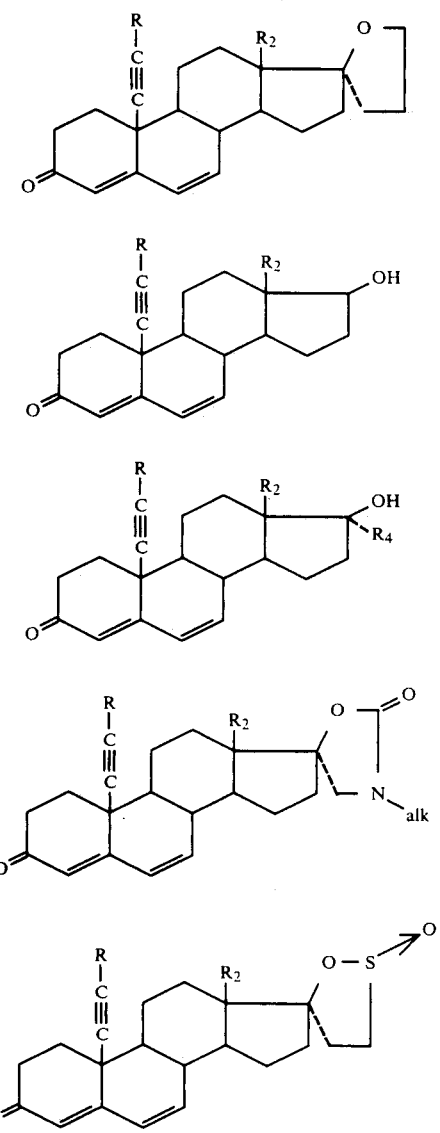

the compounds of formula $I_B$, $I_B'$, $I_B''$, $I_{3B}$, $I_{4B}$, $I_{5B}$ and $I_{6B}$ are optionally reacted with either an organomagnesium compound of the formula $R_1MgX'$ optionally in the presence of a copper salt, wherein $R_1$ has the above significance and $X'$ is halogen, or an organometallic compound of the formula $(R_1)_2CuLi$, then with an acid to obtain the following compounds of formulae $I_C$, $I_C'$, $I_C''$, $I_{4C}$, $I_{5C}$ and $I_{6C}$

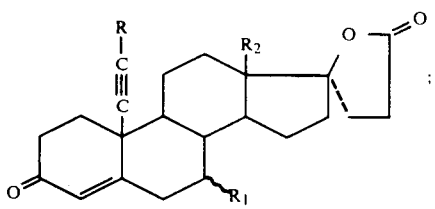

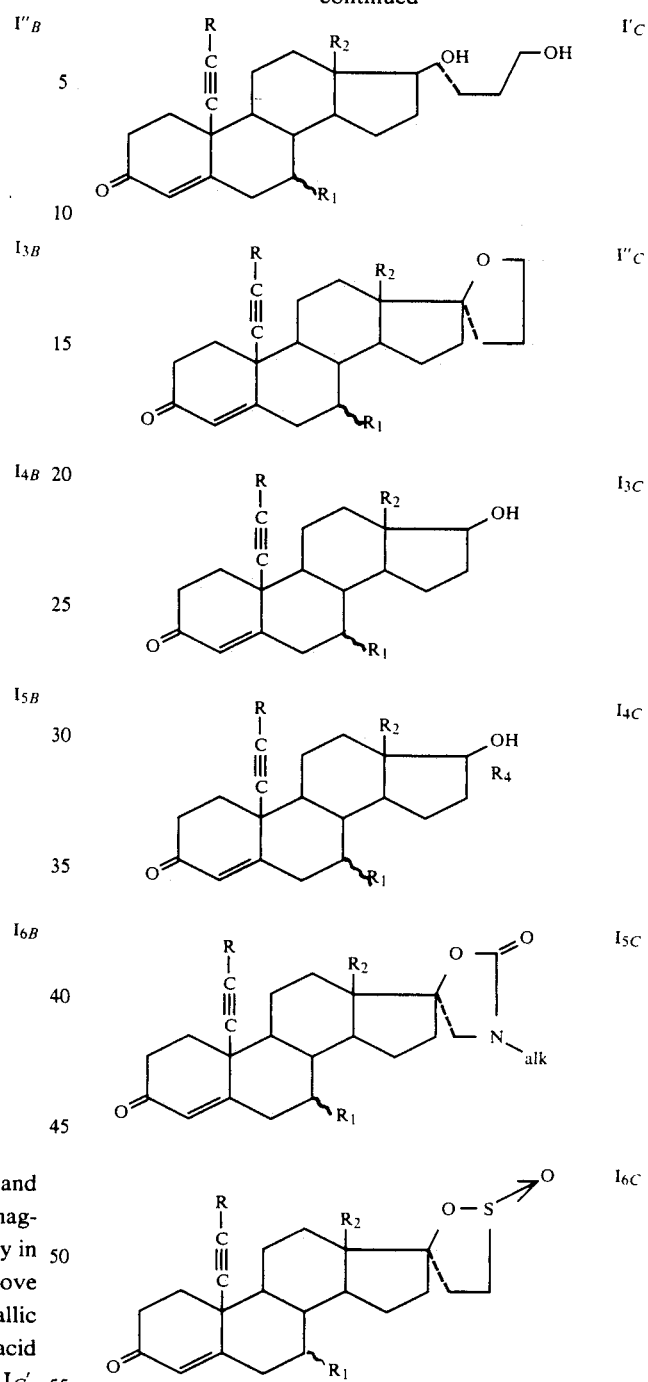

in the form of a 7α- and 7β-mixture, which mixture is optionally separated and optionally 7β products are reacted with a dehydrogenation reagent to obtain the corresponding $\Delta^{6(7)}$ products: or the compounds of formulae $I_B$, $I_B'$, $I_B''$, $I_{3B}$, $I_{4B}$, $I_{5B}$ and $I_{6B}$ are treated with a reagent chosen from the group consisting of trimethylsulfonium iodide and trimethylsulfoxonium iodide in the presence of a strong base to obtain the following compounds of formulae $I_D$, $I_D'$, $I_{3D}$, $I_{4D}$, $I_{5D}$ and $I_{6D}$

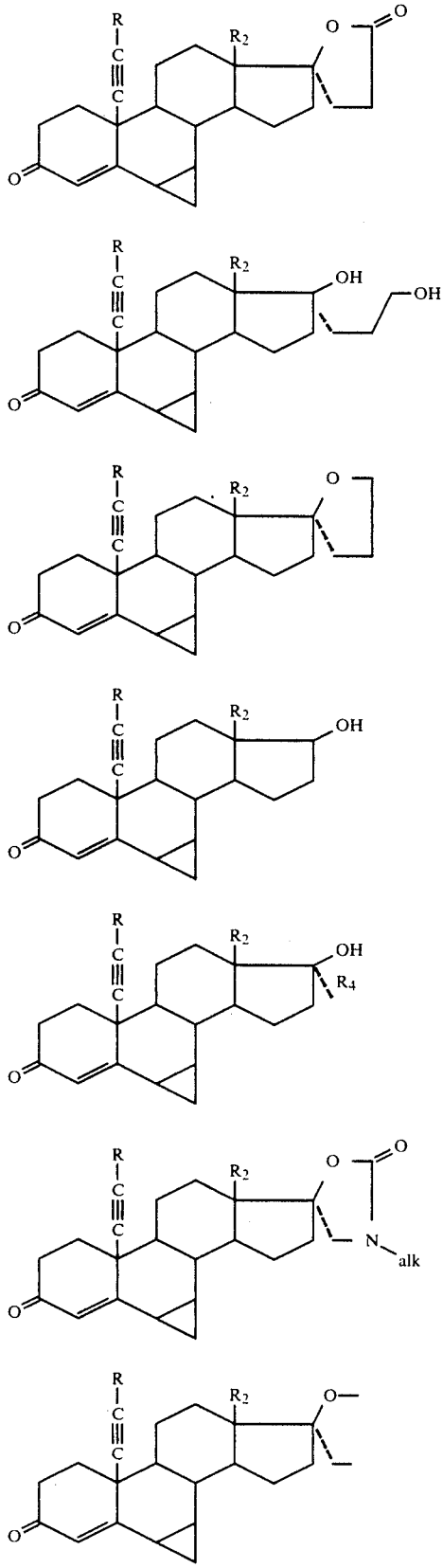

in the form of a 6α-, 7α- and 6β-, 7β- mixture, and, if desired, the isomers so obtained are separated, and op- tionally the isomers so obtained are separated, and if desired, the products

| $I_A$, | $I_A'$, | $I_A''$, | $I_{3A}$, | $I_{4A}$, | $I_{5A}$, | $I_{6A}$, |
|---|---|---|---|---|---|---|
| $I_B$, | $I_B'$, | $I_B''$, | $I_{3B}$, | $I_{4B}$, | $I_{5B}$, | $I_{6B}$, |
| $I_C$, | $I_C'$, | $I_C''$, | $I_{3C}$, | $I_{4C}$, | $I_{5C}$, | $I_{6C}$, |
| $I_D$, | $I_D'$, | $I_D''$, | $I_{3D}$, | $I_{4D}$, | $I_{5D}$, | $I_{6D}$ | are reacted with a dehydrogenation reagent or a microorganism capable of dehydrogenating the molecule in the position 1(2) to obtain the corresponding compounds having an unsaturation in position 1(2), and optionally the products of formulae $I_A$, $I_B$, $I_C$ and $I_D$ and the corresponding products having an unsaturation in position 1(2) are reacted with an alkali metal hydroxide or with ammonia to obtain the corresponding products wherein X is hydroxyl and Y is —CH₂CH₂CO₂M' and M' is an alkali metal or ammonium and optionally the products so obtained are reacted with an acid agent to obtain the compounds wherein X is hydroxyl and Y is —CH₂CH₂CO₂H, and optionally the products in which the substituent at position 10 includes R of the hydroxyalkyl type, are reacted with carbon tetrabromide or carbon tetrachloride in the presence of triphenylphosphine to obtain the corresponding brominated and chlorinated derivatives, and optionally the products with a 10-ethynyl are reacted with a halo-succinimide to obtain the corresponding products with —C≡C—Hal at position 10 and optionally the 17β- hydroxyl of the products having a hydrogen, R₄ or —CH₂—CH₂—CH₂OH at 17α position is acylated or etherified.

The protective groups of the functions which R can include, for example, the hydroxy or amino groups, are chosen from known groups. The protective group of the ketone function which K represents can be a ketal, a thioketal, an oxime or an alkoxime. It is preferred to use a ketal such as bis-methoxy or a cyclic ketal such as ethylene dioxy as these groups are eliminated in an acid medium. The trimethylsulfonium halide which is used is preferably the iodide and the strong base in the presence of which the reaction takes place is preferably potassium tertbutylate.

A metallic derivative of acetonitrile is then made to act, and this can, for example, be the lithium derivative prepared in the presence of butyllithium. The derivative so obtained which includes a 17-cyanoethyl is then reacted with a base which can, for example, be sodium hydroxide or potassium hydroxide, and the product obtained is acidified preferably with hydrochloric acid.

The reaction of allyl tetra-alkyl-phosphorodiamidate, preferably the tetra-methyl, with the compound of formula II is carried out according to the method described by STURTZ et al, Synthesis, 1980, p. 289 and the strong base in the presence of which the action takes place is preferably butyllithium. The reaction can also be done in the presence of diazabicyclooctane (DABCO) or of a crown ether. After this, acidification is effected preferably with hydrochloric acid.

The reaction of the product of the formula XMg—CH₂CH₂CH₂OB with the compound of formula II is carried out according to standard methods of preparing a magnesium derivative. B can be a usual protective group of hydroxyl such as tetrahydropyrannyl or tertbutyl. B can also be magnesium salt such as MgCl and the preparation and use of such a group is described by CAHIEZ et al, Tetr. Lett. No. 33, 1978, p. 3013.

Acidification is then effected preferably with hydrochloric acid.

The conversion of the products of formula $I_A'$ into products of formula $I_A''$ is preferably carried out in the presence of tosyl chloride and of an amine base such as pyridine. The reduction of the products of formula II into products of formula $I_{3A}$ is carried out by standard methods. For example, a hydride such as sodium borohydride can be used. The hydrolysis of the protective group K is carried out by standard methods in an acid medium, for example, by the addition of hydrochloric acid.

The addition of the magnesium compound $R_4XMg$ is carried out by standard methods. For example, the operation is effected in an anhydrous solvent such as tetrahydrofuran or ethyl ether and at a temperature lower than the ambient temperature. As for the other reactions indicated previously, an acid such as hydrochloric acid is then made to act to regenerate the ketone function in position 3.

The strong base use in the cylization leading to the product of formula $I_{5A}$ is preferably potassium hydroxide in methanol. The acid in the presence of which the reaction with the amine takes place is preferably p-toluene sulfonic acid. The trimethylsulfonium halide is preferably an iodide and the strong base used is sodium hydroxide, potassium hydroxide or potassium tertbutylate. The separation of the diastereo-isomers is carried out by the standard means of chromtography or crystallization.

The object of the reaction of an orthoformate with the products of formulae $I_A$, $I_A'$, $I_A''$, $I_{3A}$, $I_{4A}$, $I_{5A}$ and $I_{6A}$ is to prepare 3-alkoxy-$\Delta^{3,5}$ compounds of the formula

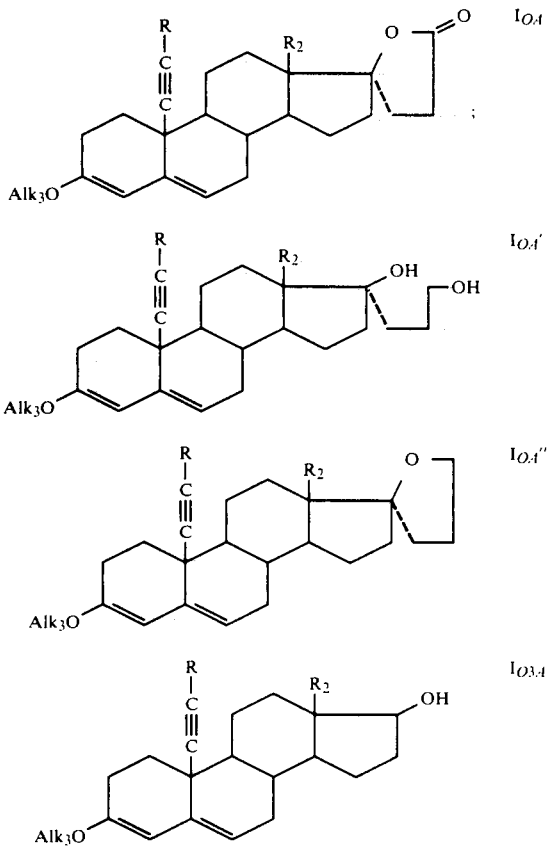

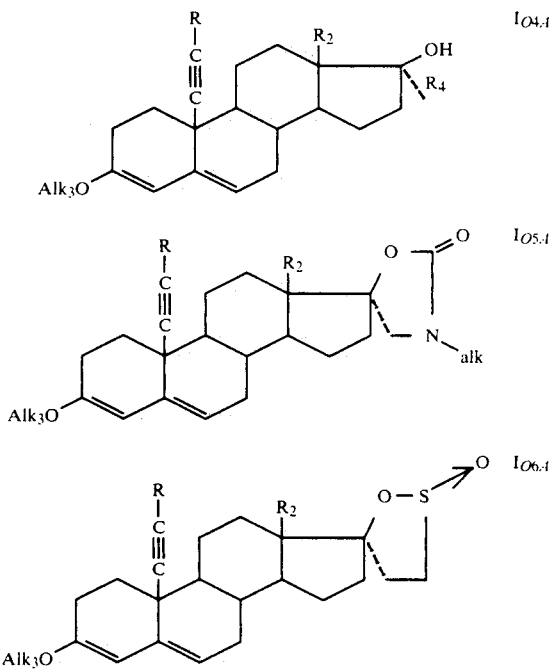

In formulae $I_{OA}$, $I_{OA}'$, $I_{OA}''$, $I_{O3A}$, $I_{O4A}$, $I_{O5A}$ and $I_{O6A}$, R, $R_2$ and $R_4$ have the above definitions and $Alk_3$ is an alkyl of 1 to 4 carbon atoms. The orthoformate used is preferably ethyl orthoformate in the presence of p-toluenesulfonic acid and the dehydrogenation agent used is preferably chloranil (tetrachloro-1,4-benzoquinone) but DDQ (2,3-dichloro-5,6-dicyano-1,4-benzoquinone) can also be used. The reaction of the product of formula $R_1MgX'$ in which X' is chlorine, bromine or iodine is preferably carried out in the presence of a cupric salt such as cupric acetate, chloride or bromide, or a cuprous salt such as cuprous chloride, bromide or iodide. The acid that is utilized after the reaction of a product with the formula $(R_1)_2CuLi$ is hydrochloric, nitric or sulfuric acid.

The possible separation of the different isomers is achieved by chromatography or by fractional crystallization. The possible dehydrogenation of the 7β- products is carried out under the conditions previously stated. The base used to form the ylide corresponding to trimethylsulfonium iodide and trimethylsulfoxonium iodide is sodium hydride or potassium tertbutylate. The possible separation is carried out according to standard methods stated above.

The conversion of the products of formulae $I_A$ to $I_{6A}$, $I_B$ to $I_{6B}$, $I_C$ to $I_{6C}$ and $I_D$ to $I_{6D}$ into products with an unsaturation at position 1(2) is preferably carried out by making the bacteria "*Arthrobacter simplex*" act biochemically but other microorganisms can also be used. In this case, the reaction is preferably carried out in a buffered aqueous medium. A chemical method can also be used by reacting the products with a derivative of p-benzoquinone or of chloranil and the reaction takes place, for example, in solution in an organic solvent such as dioxane, acetone, benzene or tertbutyl alcohol. As dehydrogenation reagent, selenious anhydride or seleninic phenyl anhydride can also be used.

The alkali metal hydroxide to which the products of formulae $I_A$, $I_B$ and $I_C$ may be submitted, as well as the corresponding product with an unsaturation in position 1(2) is preferably sodium or potassium hydroxide. The acid agent with which the products so obtained may be reacted is hydrochloric acid, sulfuric acid, nitric acid or acetic acid.

The halosuccinimide which acts with the products with 10-ethynyl is N-bromo- or N-chlorosuccinimide, preferably in the presence of silver nitrate.

The possible acylation of the products with a 17β-hydroxyl radical and a 17α-hydrogen or $R_4$ is carried out according to the usual methods. There can, for example, be used an acyl anhydride or halide such as acetic anhydride or acetyl chloride. The etherification of the same products is also carried out in the usual conditions, for example, with an alkyl halide.

The invention also has as its subject a process for the preparation of the compounds of formula $I_{3,4}$ as defined above comprising reaction of a compound of the formula

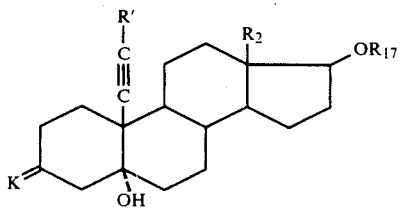

wherein K, R' and $R_2$ have the above definitions and $R_{17}$ is hydrogen or a protective group of hydroxyl with an acid and possibly with a deprotection reagent of the hydroxyl. When $R_{17}$ is a protective group of the hydroxyl, it is chosen from known groups and benzoyl and tetrahydropyrannyl are preferred. The groups are normally eliminated by acid treatment aiming to obtain the 3-ketone-$\Delta^4$. If this is not the case, the compounds of formula II' are reacted with a standard deprotection reagent. As indicated above, the preferred acid treatment is the addition of hydrochloric acid.

The compounds of the formulae II and II' used at the start of the process of the present application may be prepared by reacting a lithium compound of the formula R'—C≡C—Li act with a compound of the formula

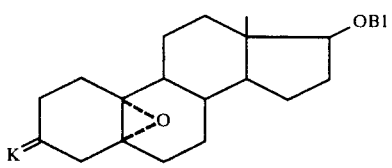

wherein $B_1$ is a protective group of the hydroxyl to obtain a compound of the formula

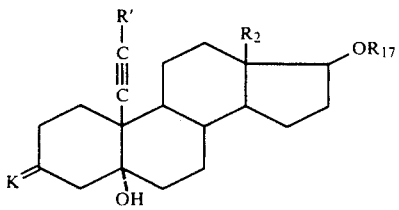

wherein $R_{17}$ is hydrogen or $B_1$ which product is submitted first to a reaction for the deprotection of the hydroxyl if the protective group has not been cleaved during the preceding reaction, then to an oxidation reaction to obtain the compounds of formula II.

The protective group which $R_1$ can be is preferably an acyl group such as benzoyl. The lithium compound R'—C≡C—Li can be prepared by the usual methods and the hydrolysis of $B_1$ can also be realized by the usual methods if the cleavage has not already taken place during the preceding reaction. Hydrolysis in a basic medium can be used. The oxidation at the position 17 is carried out, for example, by use of pyridinium chlorochromate prepared according to Tet. Letters, No 31 (1975), p. 2647 and an example of such a preparation is described in the European Pat. No. 0,023,856 (Ex. 5).

The products of formula III as well as certain products of formula II' are known in the literature or can be prepared starting from known products by analogous methods. There can be cited as source for the preparation of compounds of formula III French Pat. No. 1,550,974 and for the preparation of products of formula II' European Pat. No. EPO No. 023,856, already mentioned.

The aldosterone antagonistic and increased hydrosodic diuresis compositions are comprised of an aldosterone antagonistically and increased hydrosodic diuresis effective amount of at least one steroid of formula I and an inert pharmaceutical carrier or excipient. The compositions may be in the form of tablets, capsules, cachets, dragees granules, emulsions, syrups, suppositories and injectable preparations.

Examples of suitable excipients or carriers are talc, gum arabic, lactose, starch, magnesium stearate, cocoa butter, aqueous or non-aqueous vehicles, fatty bodies of animal or vegetable origin, paraffin derivatives, glycols, various wetting agents, dispersants and emulsifiers and preservatives.

The compositions of the invention are antagonists of aldosterone and increase the hydrosodic diuresis with conservation of the organic potassium. In addition, the compositions have the advantage of presenting only very little secondary hormone effects. Tests carried out on the receptor and in vivo have shown, in particular, that the compositions are less anti-androgenic than the previously described anti-aldosterone products and are therefore useful to combat arterial hypertension and cardiac insufficiencies.

The novel method of treating arterial hypertension and cardiac insufficiencies in warm-blooded animals, including humans, comprises administering to warm-blooded animals an amount of at least one compound of formula I sufficient to relieve arterial hypertension and cardiac insufficiencies. The compounds may be administered orally, rectally or parenterally and the usual daily dose is 0,07 to 7 mg/kg depending on the specific compound, the condition treated and the method of administration. For example, the compound of Example 1 may be administered orally at 0,1 to 2,7 mg/kg.

In the following examples there are described several preferred embodiments to illustrate the invention. However, it should be understood that the invention is not intended to be limited to the specific embodiments.

EXAMPLE 1

Gamma-lactone of 10β-ethynyl-17β-hydroxy-3-oxo-19-nor-17α-Δ⁴-pregnen 21-carboxylic acid STEP A: Cyclic 3,3-(1,2-ethanediyl) acetal of 10β-ethynyl-5α-hydroxyestran-3,17-dione At 20° C. and under an inert atmosphere, 1.9 g of cyclic 1,2-ethanediyl acetal of 10β-ethynyl-5α,17β-dihydroxy-estran-3-one [described in the European Pat. No. EP 0,023,856] were dissolved in 60 ml of acetone and then, dropwise over about 20 minutes at +5° C. 1.5 ml of Bowers reagent were added with stirring for 40 minutes at +5° C. 2 ml of isopropanol and 10 ml of ethyl acetate were added followed by washing with sodium thiosulfate, then with salt water, drying and concentrating to dryness by evaporation under reduced pressure. The 1.92 g of crude product were crystallized from a mixture of methylene chloride and isopropyl ether to obtain 1.55 g of cyclic 3,3-(1,2-ethanediyl) acetal of 10β-ethynyl-5α-hydroxy-estran-3,17-dione melting at 207° C.

Analysis: $C_{22}H_{30}O_4$; molecular weight=358.48 Calculated: % C 73.71: % H 8.43: Found: 74.0: 8.6.

IR Spectrum (chloroform)

OH in 5 at 3480 cm$^{-1}$: C≡CH at 3305 cm$^{-1}$: C=O at 1751 cm$^{-1}$.

NMR Spectrum (deuterochloroform)

Peak at 0.92 ppm (hydrogens of 18-methyl):
Peak at 8.25 ppm (hydrogen of ethynyl):
Peaks at 3.99 ppm (hydrogens of methylenes of

).

Peaks at 4.27 ppm (hydrogen of 5-hydroxyl).

STEP B: Lactonization

Under an inert atmosphere, 20.8 ml of 1.65N n-butyl-lithium in hexane were introduced at −50° C. into 21 ml of tetrahydrofuran, and over 15 minutes at −50° C., 3.52 ml of allyl-N,N,N',N'-tetramethylphosphorodiamidate in solution in 15 ml of tetrahydrofuran were added. The resulting orange-colored solution was stirred for 1 hour at −30° C. and then, over about 10 minutes at −30° C., 1.55 g of the product of Step A in solution in 30 ml of tetrahydrofuran were added. After allowing the temperature to return to 20° C. and stirring for 90 minutes at 20° C., 30 ml of a 2N aqueous solution of hydrochloric acid were introduced dropwise at +3° C. with stirring for 30 minutes at ambient temperature. Extraction was effected with ethyl acetate and the extracts were washed with salt water, then dried and concentrated to dryness under reduced pressure to obtain 2.7 g of the expected product A is obtained.

STEP C: Deketalization and dehydration

At 20° C. under an inert atmosphere, 2.7 g of the product of Step B were dissolved in 27 ml of ethanol and then 5.4 ml of an aqueous solution of 6N hydrochloric acid were added with stirring at 50° C. for 105 minutes followed by concentration to dryness under reduced pressure. Salt water was added, and extraction was done with methylene chloride. The extracts were washed with water, dried, and concentrated to dryness under reduced pressure. The 1.5 g of residue were chromatographed over silica and eluted with a mixture of petroleum ether and ethyl acetate (6/4) to obtain 900 mg of gamma-lactone of 10β-ethynyl-17β-hydroxy-3-oxo-19-nor-17α-Δ⁴-pregnen-21-carboxylic acid, 3 melting at 136° C. (impure and 260 mg of 10β-ethynyl-Δ⁴-estren-3,17-dione melting at 206° C. 1 and 110 mg of gamma-lactone of 10β-ethynyl-17α-hydroxy-3-oxo-19-nor-Δ⁴-pregnen-21-carboxylic acid melting at 265° C. 2 .

Check of product 110
IR Spectrum (chloroform)

Absence of OH: —C≡CH at 3305 cm$^{-1}$ (f) and 2100 cm$^{-1}$ 3-one: 1672 cm$^{-1}$ and 1645 cm$^{-1}$; 17-one 1735 cm$^{-1}$, Δ-⁴ 1623 cm$^{-1}$; C=C of f. 867 cm$^{-1}$.

NMR Spectrum (deuterochloroform)

Peak at 0.96 ppm (hydrogens of 18 Me);
Peak at 2.29 ppm (hydrogen of C≡CH)
Peak at 5.83 ppm (H₄).

Check of product 210
IR Spectrum (chloroform)

C≡CH at 3305 cm$^{-1}$; gamma-lactone at 1763 cm$^{-1}$ Δ$^{-4}$, 3-one 1671 cm$^{-1}$, 1624 and 866 cm$^{-1}$, NMR Spectrum (deuterochloroform)

Peak at 0.84 ppm (hydrogens of 18 Me);
Peak at 2.27 ppm (hydrogen of C≡CH);
Peak at 5.28 ppm (hydrogen H₄).
The other protons from 0.9 to 2.8 ppm Check on the product 310

The product 3 purified for analysis by crystallization from a mixture of methylene chloride and isopropyl ether to obtain 500 mg of crystallized product melting at ≃136° C. (impure).

Analysis: $C_{29}H_{28}O_3$; molecular weight=352.45 Calculated: % C 78.37: % H 8.01: Found: 78.2: 8.1: (after drying at 135° C.).

[α]$^{20}_D$: +155°5 (c=1% chloroform)

IR Spectrum (chloroform)

≡CH at 3305 cm$^{-1}$: gamma-lactone at 1764 cm$^{-1}$ Δ-$^{-4}$, 3-one dat 1672 cm$^{-1}$, 1624 cm$^{-1}$, 867 cm$^{-1}$ UV Spectrum (ethanol)
Max. 235 nm ε=16,700
Max. 314 nm ε=1,700

NMR Spectrum (deuterochloroform)
Peak at 1.08 ppm (hydrogens of 18-Me);
Peak at 2.30 ppm (hydrogen of C≡CH);
Peak at about 5.81 ppm (hydrogen H₄).
Peaks from 0.9 to 2.8 ppm, the other protons,

EXAMPLE 2

17β-hydroxy-10β-(1-propynyl)-Δ⁴-estrene-3-one

STEP A: 1,2-ethanediyl cyclic acetal of 10β-ethynyl-5α-hydroxy-17β-(2H-tetrahydropyrannyl-2-oxy)-estran-3-one At 20° C., 3.75 g of 1,2-ethanediyl cyclic acetal of 10β-ethynyl-5α,17β-dihydroxy-estran-3-one, 37 ml of tetrahydrofuran, 10 ml of dihydropyran and 0.2 ml of POCl₃ were mixed together and the resultant yellow solution was stirred 90 minutes at 20° C. The reaction mixture was poured into 150 ml of water and was extracted with methylene chloride. The extracts were washed with water, dried and concentrated to dryness under reduced pressure. The 6.15 g of residue were chromatographed over silica and eluted with a mixture of petroleum ether and ethyl acetate (8/2)+1 per mil of triethylamine to obtain 4.45 g of 1,2-ethanediyl cyclic acetal of 10β-ethynyl-5α-hydroxy-17β-(2H-tetrahydropyrannyl-2-oxy)-estran-3-one melting at about 100° C.

IR Spectrum (chloroform):

Absence of OH at position 17: OH at position 5 at 3485 cm$^{-1}$, —C≡CH at 3305 cm$^{-1}$ (f) and 2100 cm$^{-1}$(f).

NMR Spectrum (deuterochloroform+1 drop of C$_5$D$_5$M)

Peaks at 0.82 and 0.83 ppm (hydrogens of 18-methyl);
Peak at 2.24 ppm (hydrogen of ethynyl):
Peak of 3.33 ppm to 4.0 ppm (hydrogens of

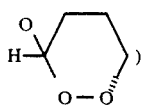

Peak at 3.94 ppm (hydrogens of methylenes of

Peak at 4.23 ppm (hydrogen of 5-hydroxyl)
Peak at 4.64 ppm (hydrogen of )

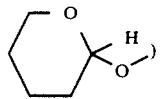

STEP B: 1,2-ethanediyl cyclic acetal of 5α-hydroxy-10β-(1-propynyl)-17β-(2H-tetrahydropyrannyl-2-oxy)-estran-3-one At 20° C. and under an inert atmosphere, 4.42 g of the product of Step A were dissolved in 40 ml of tetrahydrofuran and 13.7 ml of 1.6M n-butyllithium in tetrahydrofuran were added. The temperature was brought back to 20° C. and 3.1 ml of methyl iodide were added. The reaction mixture rose from 20° to 33° C., and a colorless solution was obtained which was stirred for 45 minutes. Then, at +3° C., 20 ml of an aqueous solution of ammonium chloride were added and the reaction mixture was decanted and extracted with ethyl acetate. The extracts were washed with salt water, dried and concentrated to dryness under reduced pressure. The 4.47 g of residue were chromatographed over silica and eluted with a mixture of petroleum ether and ethyl acetate (8-2)+1 per mil of triethylamine to obtain 3.9 g of 1,2-ethanediyl cyclic acetal of 5α-hydroxy-10β-(1-propynyl)-17β-(2H-tetrahydropyrannyl-2-oxy)-estran-3-one melting at 113° C.

IR Spectrum (chloroform)
OH at position 5 at 3485 cm$^{-1}$.
NMR Spectrum (deuterochloroform)
Peaks at 0.8 and 0.82 ppm (hydrogens of 18 methyl);
Peak at 1.85 ppm (methyl of propenyl);
Peak at 3.33 ppm and 4 ppm (hydrogens of

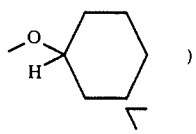

Peak at 4.64 ppm (hydrogen of

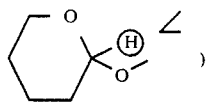

STEP C:
17β-hydroxy-10β-(1-propynyl)-Δ$^4$-estren-3-one

Under an inert atmosphere, 1 g of 1,2-ethanediyl cyclic acetal of 5α-hydroxy-10β-(1-propynyl)-17β-(2H-tetrahydropyrannyl-2-oxy)-estran-3-one was suspended in 10 ml of ethanol and 2 ml of an aqueous solution of 6N hydrochloric acid. The mixture was heated to 50° C. to obtain a solution at the end of about 15 minutes. The solution was stirred for 5 hours and 15 minutes at 50° C. and the ethanol was eliminated by distilling under reduced pressure. The residue was taken up in water and was extracted with methylene chloride. The extracts were washed with water, dried, and concentrated to dryness by distilling under reduced pressure. The 840 mg of residue were chromatographed over silica and eluted with a mixture of cyclohexane and ethyl acetate (1/1) to obtain 570 mg of 17β-hydroxy-10β-(1-propynyl)-Δ$^4$-estren-3-one melting at 172° C.

570 mg of the product were crystallized for microanalysis from a mixture of methylene chloride and isopropyl ether to obtain 520 mg of the product melting at 172° C.

Analysis: C$_{21}$H$_{28}$O$_2$; molecular weight=312.45 Calculated: % C 78.1: % H 8.8: Found: 78.3: 9.1.
IR Spectrum (chloroform)
OH at 3612 cm$^{-1}$: conjugated ketone at 1667 cm$^{-1}$;
—C=C— at 1622 cm$^{-1}$
UV Spectrum (ethanol)
Max 235 nm; ε=15,700
NMR Spectrum (deuterochloroform)
Peak at 0.84 ppm (hydrogens of 18-methyl):
Peak at 1.88 ppm (hydrogens of methyl of propynyl);
Peak at 3.66 ppm (17-hydrogen);
Peak at 5.78 ppm (4-hydrogen).

EXAMPLE 3

γ-lactone of 17β-hydroxy-3-oxo-10β-(1-propynyl)-19-nor-17α-Δ$^4$-pregnene-21-carboxylic acid STEP A: 3,3-(1,2-ethanediyl)cyclic acetal of 5α-17β dihydroxy-10β-(1-propynyl)-estran-3-one.

Under an inert atmosphere, 2.2 g of 1,2-ethanediyl cyclic acetal of 5α-hydroxy-10β-(1-propynyl)-17β-(2H-tetrahydropyrannyl-2-oxy)-estran-3-one were dissolved at 120° C. in 44 ml of acetic acid and 11 ml of water were added with stirring for 35 minutes at 20° C. Then the acetic acid was eliminated by distillation under reduced pressure and an aqueous solution of sodium bicarbonate was added for neutralizing. Then extraction was effected with ethyl acetate and the extracts were washed with salted water, dried, and concentrated to dryness under reduced pressure. The 2.3 g of residue were chromatographed over silica and eluted with mixtures of cyclohexane and ethyl acetate (7/5) then (1/1) to obtain 700 mg of 3,3-(1,2-ethanediyl)-cyclic acetal of 5α-17β-dihydroxy 10β-(1-propynyl) estran-3-one as well as 715 mg of the starting product, 225 mg of 5α-hydroxy-10β-(1-propynyl)-17β-hydroxyestran-3-one (IV) and 200 mg of 5α, 17β-dihydroxy-10β-(1-propynyl)-estran-3-one (III).

Check of Product (II)
R Spectrum (chloroform)
OH at position 17 at 3609 cm$^{-1}$; OH at position 5 at 3480 cm$^{-1}$.
NMR Spectrum (deuterochloroform with 1 drop of C$_5$O$_5$N).
Peak at 0.8 ppm (hydrogens of 18-methyl);
Peak at 1.86 ppm (hydrogens of the propynyl methyl);
Peak at 2.97 ppm and 4.2 ppm (hydrogens of 5and 17-hydroxyls);
Peaks at 3.58-3.66-3.75 ppm (17-hydrogen).
Check of product (IV):
IR Spectrum (chloroform)
OH: 3305 cm$^{-1}$ (free)+a little associated: C=O: 1709 cm$^{-1}$;
NMR Spectrum (deuterochloroform)
Peaks at 0.83-0.85 ppm (hydrogens of 18-methyl);
Peak at 1.91 ppm (hydrogens of propynyl methyl);
Peaks from 3.33 to 4.11 ppm (hydrogens of

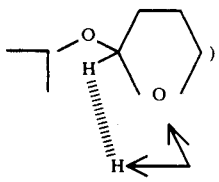

Peak at 4.64 ppm (hydrogen of

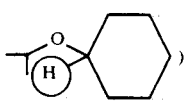

Check of product (III)
IR Spectrum (chloroform)
OH free, 3609 cm$^{-1}$+associated. C=O 1709 cm$^{-1}$.
NMR Spectrum (deuterochloroform)
Peak at 0.83 ppm (hydrogens of 18-methyl);
Peak at 1.93 ppm (hydrogens of propynyl methyl);
5 Peaks at 3.59-3.67-3.74 ppm (17-hydrogen).

STEP B: 3-3-(1,2-ethanediyl) cyclic acetal of 5-α-hydroxy-10β(1-propynyl)-estran-3,17-dione Under an inert atmosphere and at 20° C., 990 mg of the product of Step A were dissolved in 30 ml of acetone and then, at +3° C., 0.92 ml of Bowers reagent was added dropwise with stirring for 90 minutes at +3° C. The reaction mixture was poured into sodium bicarbonate solution and then was extracted with ethyl acetate The extracts were washed with salted water, dried, concentrated to dryness under reduced pressure to obtain 1 g of dry residue which was chromatographed over silica. Elution with a mixture of cyclohexane and ethyl acetate (7/3) with 1% of triethylamine yielded 860 mg of 3,3-(1,2-ethanediyl) cyclic acetal of 5α-hydroxy-10β-(1-propynyl)-estran-3,17-dione melting at 172° C.

A 125 mg sample was crystallized for analysis from a mixture of methylene chloride and isopropyl ether to obtain 85 mg of the product melting at 172° C.
Analysis: Calculated: % C 74.16: % H 8.66: Found: 74.1: 8.7:
IR Spectrum (chloroform):
OH at position 5 3488 cm$^{-1}$: 1-keto 1731 cm$^{-1}$;
NMR Spectrum (deuterochloroform)
Peak at 0.91 ppm (hydrogens of 18-methyl);
Peak at 1.85 ppm (hydrogens of propynyl methyl);
Peak at 3.98 ppm (hydrogens of methylenes of

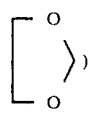

Peak at 4.22 ppm (hydrogen of 5-hydroxyl)

STEP C: γ-lactone of 17β-hydroxy-3-oxo-10β-(1-propynyl)-19-nor-17α-Δ$^4$-pregnen-21-carboxylic acid (A) Lactonization
12 ml of tetrahydrofuran were added at −50° C. to 12 ml of a 1.65N n-butyllithium solution in hexane and over about 15 minutes at −50° C., there were introduced 2.06 ml of allyl N,N,N',N'-tetramethylphosphoramidate in solution in 8 ml of tetrahydrofuran. The mixture was stirred at −30° C. for 1 hour and then, over about 10 minutes at −30° C. 880 mg of the product of Step B were added. The temperature was allowed to return to 20° C. with stirring for 1 hour. At +3° C., 20 ml of a 2N aqueous solution of hydrochloric acid were introduced with stirring at 20° C. for about 30 minutes. Then, after decanting and washing with salt water, extraction was effected with ethyl acetate. The extracts were washed with water, dried and concentrated to dryness under reduced pressure to obtain 2 g of dry residue.

(B) Deketalization and dehydration
Under an inert atmosphere, the 2 g isolated above were dissolved in 40 ml of ethanol and 4 ml of a 6N aqueous solution of hydrochloric acid were added. The mixture was heated to 60° C. for 3½ hours and the ethanol was distilled off under reduced pressure. The residue was taken up in methylene chloride, washed with water, dried and concentrated to dryness under reduced pressure. The 1.2 g of residue were purified by chromatography over silica and elution with a mixture of petroleum ether and ethyl acetate, 6/4, then with a mixture of petroleum ether and ethyl acetate 1/1 to obtain 415 mg of the crude of γ-lactone of 17β-hydroxy-3-oxo-10β-(1-propynyl)-19-nor-17α-Δ$^4$-pregnen-21-carboxylic acid melting at 234° C. The product was crystallized from a mixture of methylene chloride and isopropyl ether to obtain 361 mg of pure product melting at 235° C.
Analysis: C$_{24}$H$_{30}$O$_3$; molecular weight=366.51 Calculated: % C 78.65: % H 8.25: Found: 78.5: 8.4:
IR Spectrum (chloroform)
γ-lactone C=O at 1764 cm$^{-1}$, 3-keto-Δ$^4$ at 1669, CN 1623 cm$^{-1}$.
NMR Spectrum (deuterochloroform)
Peak at 1.03 ppm (hydrogens of 18-Me);
Peak at 1.88 ppm (hydrogens of CH$_3$—C≡C);
Peak at 5.79 ppm (4-hydrogen).

In addition there was obtained 290 mg of 10β-(1-propynyl)-Δ⁴-estren-3,17-dione melting at 212° C.
IR Spectrum (chloroform)
17-keto at 1733 cm$^{-1}$; 3-keto-Δ⁴ 1660–1622 cm$^{-1}$
NMR Spectrum (deuterochloroform)
Peak at 0.96 ppm (hydrogens of 18-Me);
Peak at 1.87 ppm (hydrogens of ≡C-Me);
Peak at 5.69 ppm (4-hydrogen), and 30 mg of γ-lactone of 17α-hydroxy-3-oxo-10β-(1-propynyl)-19-nor-Δ⁴-pregnen-21-carboxylic acid melting at 188° C.
IR Spectrum (chloroform)
C=O of γ-lactone 1762 cm$^{-1}$, 3-keto-Δ⁴-: 1669 and 1662 cm$^{-1}$
NMR Spectrum (deuterochloroform)
Peak at 0.83 ppm (hydrogens of 18-Me);
Peak at 1.88 ppm (hydrogens of CH₃—C≡C);
Peak at 5.79 ppm (4-hydrogen).

EXAMPLE 4

Pharmaceutical composition

Tablets were prepared containing 50 mg of the product of Example 1 and sufficient excipient of talc, starch, magnesium stearate for a final weight of 100 mg

PHARMACOLOGICAL STUDY

Study of the anti-aldosterone activity of the mineralo-corticoid receptor of the rat kidney Male Sprague-Dawley EOPS rats weighing 140 to 160 g, suprarenalectomized 4 to 6 days earlier, were killed and their kidneys were perfused in situ with 50 ml of Tris 10 mM-saccharose 0.25M buffer, HCl pH 7.4. The kidneys were then removed, decapsulated and homogenized at 0° C. with a Potter polytetrafluoroethylene glass (1 g of tissue for 3 ml of buffer). The homogenate was centrifuged for 10 minutes at 800 g at 0° C. To eliminate the fixation of the tritiated aldosterone on the glucocorticoid receptor, 11β,17β-dihydroxy-17α-(1-propynyl)-Δ$^{1,4,6}$-androstatrien-3-one which fixes uniquely on the glucocorticoid receptor was added to the supernatant at a final concentration of 10$^{-6}$M. This supernatant was ultracentrifuged at 105,000 g for 60 minutes at 0° C. and aliquots of the supernatant were incubated at 0° C. with a constant concentration (T) of tritiated aldosterone in the presence of increasing concentrations (0–2500×10$^{-9}$M) of cold aldosterone or of the cold product under study. After an incubation time (t), the concentration of tritiated aldosterone bound (B) was measured by the technique of adsorption on charcoal-dextran.

The calculation of the relative liaison affinity (RLA) was carried out as follows: The two following curves were drawn: the percentage of tritiated hormone bonded B/T as a function of the logarithm of the concentration of the cold reference hormone, and B/T as a function of the logarithm of the concentration of the cold product under test. The straight line of the equation I₅₀=(B/T max+B/T min)/2 was determine B/T max=percentage of the tritiated hormone bonded for an incubation of this triated hormone at the concentration (T), B/T min=percentage of the tritiated hormone bonded for an incubation of this tritiated hormone at the concentration (T) in the presence of a great excess of cold hormone (2500.10$^{-9}$M). The intersections of the straight line I₅₀ and the curves enabled the concentrations of the cold reference hormone (CH) and of the cold product tested (CX) to be evaluated which inhibited by 50% the bonding of the tritiated hormone on the receptor. The relative liaison affinity (RAL) of the product tested is determined by the equation:

$$RAL = 100 \frac{(CH)}{(CX)}$$

The following results were obtained;

| Product Example | Incubation time at 0° C. | |
|---|---|---|
| | 1 hour | 24 hours |
| 1 | 125 | 65 |
| 3 | 50 | 43 |

Various modifications of the products and methods of the invention may be made without departing from the spirit or scope thereof and it is to be understood that the invention is intended to be limited only as defined in the appended claims.

What we claim is:
1. 10β-alkynyl-steriods of the formula

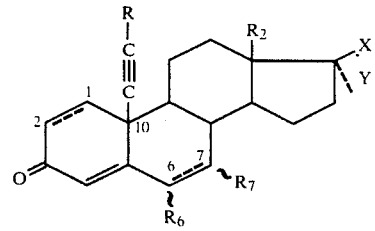

wherein R is selected from the group consisting of hydrogen, alkyl and alkoxy of 1 to 8 carbon atoms, alkenyl and alkynyl of 2 to 8 carbon atoms substituted alkyl of 1 to 8 carbon atoms, substituted alkenyl and alkynyl of 2 to 8 carbon atoms, said substituents being selected from the group consisting of —OH, carboxy, methoxycarbonyl, ethoxycarbonyl, amino, tritylamino, chloroacetylamino, trifluoroacetylamino, trichloroethoxycarbonylamino, methylamino, dimethylamino and halogen, unsubstituted or substituted aryl and aralkyl with at least one member of the group consisting of —OH, carboxy, methoxycarbonyl, ethoxycarbonyl, amino, methylamino, dimethylamino, methoxy, methyl and methylthio, carboxy, esterified carboxy, dialkylamino with alkyl of 1 to 6 carbon atoms, halogen and trialkylsilyl of 1 to 7 alkyl carbon atoms, R₆ and R₇ taken together with the carbon atoms to which they are attached form cyclopropyl or R₆ is hydrogen and R₇ is R₁, R₁ is selected from the group consisting of hydrogen, unsubstituted or substituted alkyl of 1 to 6 carbon atoms, unsubstituted or substituted alkenyl and alkynyl of 2 to 6 carbon atoms and acetylthio, said substituents being at least one member of the group consisting of —OH, carboxy, methoxycarbonyl, ethoxycarbonyl, amino, tritylamino, chloroacetylamino, trifluoroacetylamino, trichloroethoxycarbonylamino, methylamino, dimethylamino and halogen, R₂ is methyl or ethyl, X and Y taken together with the carbon atoms to which they are attached form a member selected from the group consisting of

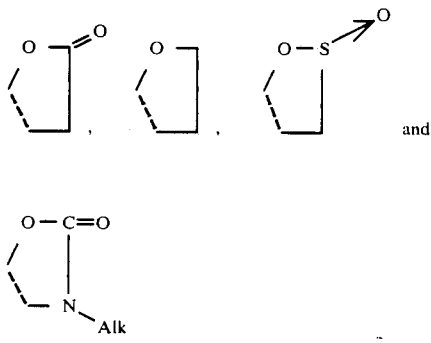

Alk is alkyl to 12 to 8 carbon atoms the dotted lines indicate the optional presence of a second carbon-carbon bond when $R_6$ and $R_7$ and the carbon to which they are attached do nòt form cyclopropyl and the wavy lines indicate that $R_6$ and $R_7$ may be in the $\alpha$ or $\beta$ position.

2. A composition having aldosterone antagonistic activity and increased hydrosodic diuresis comprising an amount of at least one compound of claim 1 sufficient to induce aldosterone antagositic activity and hydrosodic diuresis and an inert pharmaceutical carrier.

3. A compound of claim 1 having the formula

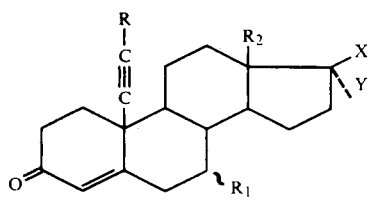

wherein R, $R_1$, $R_2$, X, Y, the wavy lines and the dotted lines have the above definition.

4. A compound of claim 1 wherein the substituent which R and $R_1$ can have are selected from the group consisting of —OH, methoxycarbonyl, ethoxycarbonyl or carboxy, $NH_2$, protected amino, halogen and mono and dialkylamino.

5. A compound of claim 1 wherein R is selected from the group consisting of hydrogen alkyl of 1 to 3 carbon atoms, phenyl and hydroxymethyl.

6. A compound of claim 1 wherein $R_1$ is selected from the group consisting of hydrogen, alkyl of 1 to 4 carbon atoms and acetylthio and X and Y form

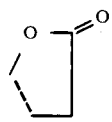

7. A compound of claim 1 which is $\gamma$-lactone of 10$\beta$-ethynyl-17$\beta$-hydroxy-3-oxo-19-nor-17$\alpha$-$\Delta^4$-pregnen-21-carboxy acid.

8. A method of inducing aldosterone antagonistic activity and hydrosodic diuresis in warm-blooded animals comprising administering to warm-blooded animals an amount of at least one compound of claim 1 sufficient to induce aldosterone antagonistic activity and hydrosodic diuresis.

9. A compound of claim I which is the $\gamma$-lactone of 17$\beta$-hydroxy-3-oxo-10$\beta$-(1-propynyl)-19-nor-17$\alpha$-$\Delta^4$-pregnene-21-carboxylic acid.

10. A method of claim 8 wherein the active compound is $\gamma$-lactone of 17$\beta$-hydroxy-3-oxo-b 10$\beta$-(1-propynyl)-19-nor-17$\alpha$-$\Delta^4$-pregnene-21-carboxylic acid.

11. A method of claim 8 wherein the active compound is $\gamma$-lactone of 10$\beta$-ethynyl-17$\beta$-hydroxy-3-oxo-19-nor-17$\alpha$-$\Delta^4$-pregnene-21-carboxylic acid.

12. A composition of claim 2 having the formula

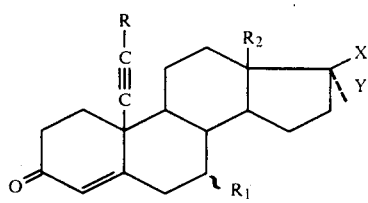

wherein R, $R_1$, $R_2$, X, Y, the wavy lines and the dotted lines have the above definition.

13. A compound of claim 2 wherein the substitutent which R and $R_1$ can comprise are selected from the group consisting of —OH, methoxycarbonyl ethoxycarbonyl or carboxy, $NH_2$, protected amino, halogen and mono and dialkylamino.

14. A composition of claim 2 wherein R is selected from the group consisting of hydrogen, alkyl of 1 to 3 carbon atoms, phenyl and hydroxymethyl.

15. A composition of claim 2 wherein $R_1$ is selected from the group consisting of hydrogen, alkyl of 1 to 4 carbon atoms and acetylthio and X and Y form

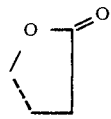

16. A composition of claim 2 wherein the active compound is $\gamma$-lactone of 10$\beta$-ethynyl-17$\beta$-hydroxy-3-oxo-19-nor-17$\alpha$-$\Delta^4$-pregnen-21-carboxylic acid.

17. A method of claim 8 wherein $R_1$ is hydrogen, alkyl of 1 to 4 carbon atoms and acetylthio, and X and Y form

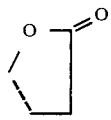

18. A composition of claim 2 wherein the active compound is $\gamma$-lactone of 17$\beta$-hydroxy-3-oxo-10$\beta$-(1-propynyl)-19-nor-17$\alpha$-$\Delta^4$-pregnene-21-carboxylic acid.

19. A method of claim 8 wherein R is selected from the group consisting of hydrogen, alkyl of 1 to 3 carbon atoms, phenyl and hydroxymethyl.

20. A compound of claim 8 wherein the substituent which R and $R_1$ can comprise are selected from the group consisting of —OH, methoxycarboyl, ethoxycarbonyl or carboxy, $NH_2$, protected amino, halogen and mono and dialkylamino.

* * * * *